United States Patent
Hung

(10) Patent No.: US 7,597,667 B2
(45) Date of Patent: Oct. 6, 2009

(54) METHOD FOR JUDGING IRREGULAR HEARTBEAT

(75) Inventor: Ching-Hsi Hung, Taipei (TW)

(73) Assignee: Rossmax International Ltd., Taipei (TW)

( * ) Notice: Subject to any disclaimer, the term of this patent is extended or adjusted under 35 U.S.C. 154(b) by 665 days.

(21) Appl. No.: 11/383,712

(22) Filed: May 16, 2006

(65) Prior Publication Data
US 2007/0270700 A1 Nov. 22, 2007

(51) Int. Cl.
*A61B 5/02* (2006.01)
(52) U.S. Cl. ...................................... 600/508
(58) Field of Classification Search ........................ None
See application file for complete search history.

(56) References Cited

U.S. PATENT DOCUMENTS

| | | | | |
|---|---|---|---|---|
| 2003/0023178 A1* | 1/2003 | Bischoff et al. | ............. | 600/515 |
| 2005/0251054 A1* | 11/2005 | Zhirnov et al. | ............. | 600/509 |
| 2005/0251056 A1* | 11/2005 | Gribkov et al. | ............. | 600/509 |
| 2006/0094967 A1* | 5/2006 | Bennett et al. | ............. | 600/508 |

FOREIGN PATENT DOCUMENTS

| | | |
|---|---|---|
| TW | 522004 | 3/2003 |
| TW | 555545 | 10/2003 |
| WO | WO 2005110215 A2 * | 11/2005 |

* cited by examiner

*Primary Examiner*—Carl H. Layno
*Assistant Examiner*—Jon-Eric C. Morales
(74) *Attorney, Agent, or Firm*—Chun-Ming Shih

(57) ABSTRACT

A method for judging irregular heartbeat performs a measurement step to measure a plurality of heartbeat pulses within a time period for a user, and to measure inter-pulse durations and total pulse numbers. The method further performs a calculation step to calculate an averaged inter-pulse duration and a heartbeat number. Afterward, the method performs a first-stage judgment step to judge whether the measured pulse number is sufficient. When the first-stage judgment step is matched, a second-stage judgment step is performed. The second-stage judgment step judges irregular heartbeat condition by comparing the averaged inter-pulse duration with each inter-pulse duration. Finally, this method performs a display step to show a sign of irregular heartbeat when the irregular heartbeat condition is matched. This method can solve inaccuracy problem due to preset threshold.

12 Claims, 4 Drawing Sheets

METHOD FOR JUDGING IRREGULAR HEARTBEAT

BACKGROUND OF THE INVENTION

1. Field of the Invention

The present invent relates to a method for judging irregular heartbeat, especially to a method for judging irregular heartbeat with higher accuracy.

2. Description of Prior Art

More than 90% of the patients of sudden death are reported to be caused by Ventricular Tachycardia (VT) or Ventricular Fibrillation (VF). Therefore, the detection of irregular heartbeat is important for preventing heart disease.

The current technology for measurement of irregular heartbeat uses Holter ambulatory ECG and Electrocardiogram, ECG. However, those services are generally conducted in professional medical institution, which is expensive for user. Therefore, the function of irregular heartbeat measurement is integrated into certain electronic sphygmomanometer for user to measure blood pressure and heart beat.

Taiwan Patent No. 522004 with title "Method and apparatus for non-invading measurement of blood pressure and heart beat" provides a method for measuring blood pressure by artery pulse. The inter-pulse duration value is measured with blood pressure and recorded in storage unit. The stored inter-pulse duration value is compared with a predetermined reference. When the stored inter-pulse duration value exceeds a predetermined reference or has a specific pattern, the patient can be judged to have irregular heartbeat.

Moreover, Taiwan Patent No. 555545 with title "System for judging irregular heartbeat with Electrocardiogram" provides a medical judgment. The system takes a time record from a long-term database of a patient and a real-time measurement of electrocardiogram from the patient. The data is processed by re-sampling, noise-removing and signal shift and then compared with a pathology database. The comparison result is used for medical evaluation.

The above-mentioned prior art methods compares measured electrocardiogram signal and pulse signal with a standard condition to generated an averaged parameter. However, the patient has different heart beat characteristics. Therefore, the above-mentioned prior art methods are not applied to all users. The setting of standard condition will also influence measurement results.

SUMMARY OF THE INVENTION

The present invention is to provide a method for judging irregular heartbeat with higher accuracy.

Accordingly, the present invention provides a method for judging irregular heartbeat. The method performs a measurement step to measure a plurality of heartbeat pulses within a time period for a user, and to measure inter-pulse durations and total pulse numbers. The method further performs a calculation step to calculate an averaged inter-pulse duration and a heartbeat number. Afterward, the method performs a judgment step to judge an irregular heartbeat condition by comparing the averaged inter-pulse duration with each inter-pulse duration. Finally, this method performs a display step to show a sign of irregular heartbeat when the irregular heartbeat condition is matched, or show a sign of no irregular heartbeat when the irregular heartbeat condition is not matched.

BRIEF DESCRIPTION OF DRAWING

The features of the invention believed to be novel are set forth with particularity in the appended claims. The invention itself however may be best understood by reference to the following detailed description of the invention, which describes certain exemplary embodiments of the invention, taken in conjunction with the accompanying drawings in which:

DETAILED DESCRIPTION OF THE INVENTION

Figure 1:
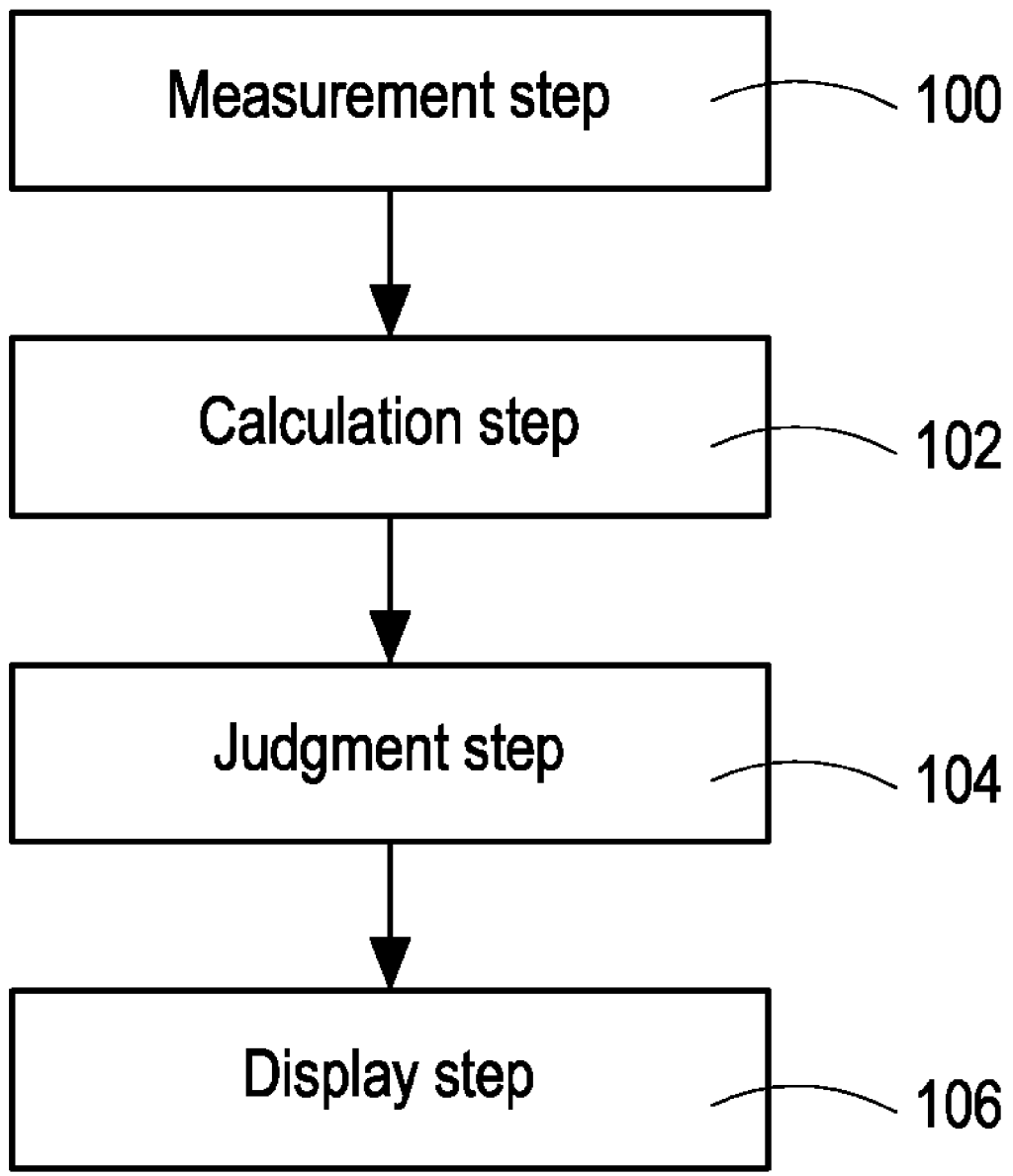
FIG. 1 shows a flowchart of the judgment steps according to the present invention.
Figure 2:
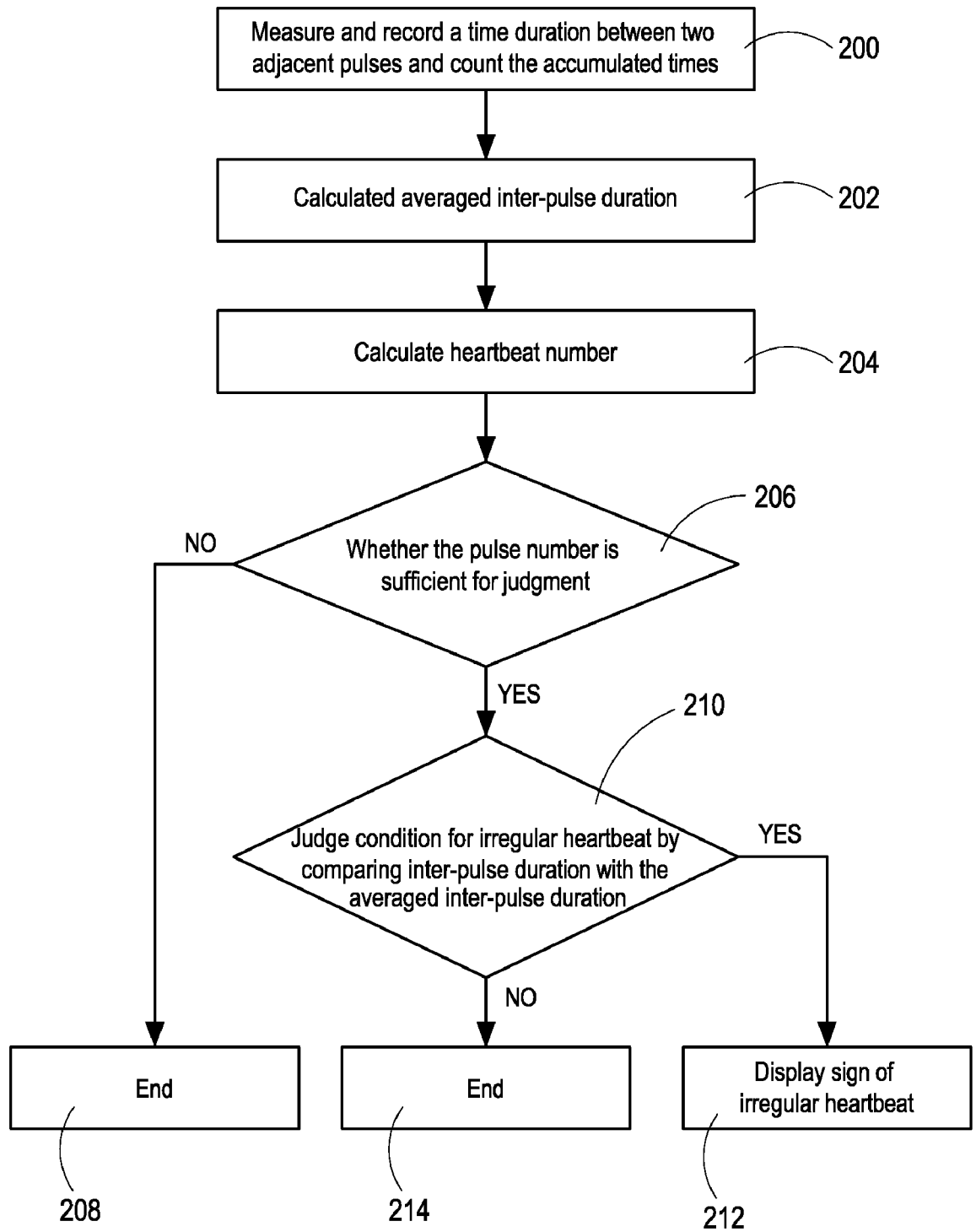
FIG. 2 shows another flowchart of the judgment steps according to the present invention.
Figure 3:
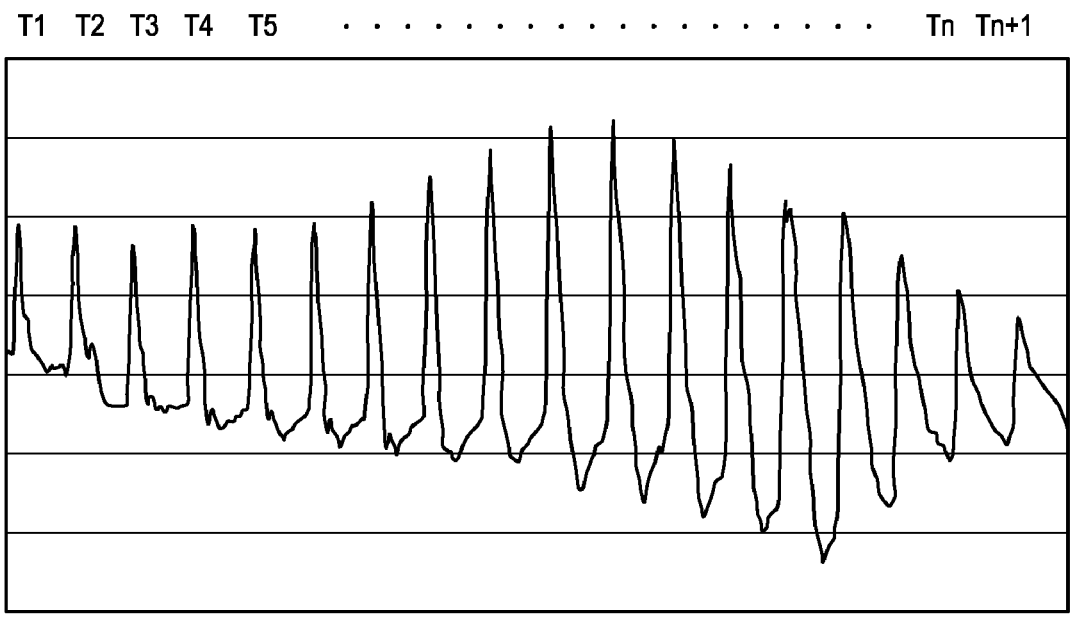
FIG. 3 shows the heartbeat pattern measured by cuff.

With reference to FIGS. 1 to 3, the method for judging irregular heartbeat according to the present invention measures the irregular heartbeat according to the data within a time period.

Step 100 is a measurement step, where the heart beat number is also measured when the user is measured with blood pressure. The inter-pulse duration ($\Delta T$) between two pulses and the accumulated pulse number are also recorded, as can be seen in step 200 of FIG. 2.

The inter-pulse duration ($\Delta T$) between two pulses is the time difference between two adjacent pulses.

$\Delta T1 = T2 - T1$ is the time duration difference between the first pulse and the second pulse.

$\Delta T2 = T3 - T2$ is the time duration difference between the second pulse and the third pulse.

$\Delta T3 = T4 - T3$ is the time duration difference between the third pulse and the fourth pulse.

$\Delta Tn = T(n+1) - Tn$ is the time duration difference between the n-th pulse and the (n+1)th pulse.

Step 102 performs a calculation step.

The averaged inter-pulse duration is calculated according to the result above, as shown in step 202 of FIG. 2. The averaged inter-pulse duration (T)=the sum of total measured inter-pulse duration divided by the total pulse number (N), as shown in formula 1.

$$T = \frac{\Delta T1 + \Delta T2 + \Delta T3 + \Delta T4 + \ldots + \Delta Tn}{N} \tag{1}$$

Afterward, the heartbeat number (H) is calculated according to the averaged inter-pulse duration (T), as shown in step 204 of FIG. 2:

$$\text{Heartbeat } (H) = \frac{60}{\text{Average inter pulse time } (T)} (\text{time/min}) \tag{2}$$

Step 104 performs a judgment step for the first-stage judgment. As shown in step 206 of FIG. 2, the step 206 judges whether the total number of irregular heartbeat reaches a predetermined number Z. When the number of irregular heartbeat is smaller than Z, the judgment step is finished in step S208.

Step 210 performs the second-stage judgment when the number of irregular heartbeat is judged to be larger than Z. Each of the inter-pulse durations is compared with the averaged inter-pulse duration (T). The second-stage judgment judges whether the inter-pulse duration is an abnormal inter-pulse duration, which exceeds the averaged inter-pulse duration by a predetermined ratio. The second-stage judgment further judges whether the number of the abnormal inter-pulse duration exceeds a predetermined count.

Step 106 performs a display step to show a sign of irregular heartbeat when the above-mentioned second-stage judgment for irregular heartbeat is matched, as shown in step 212 of FIG. 2. When the above-mentioned second-stage judgment for irregular heartbeat is not matched, step 212 of FIG. 2 shows a sign of no irregular heartbeat.

Figure 4:
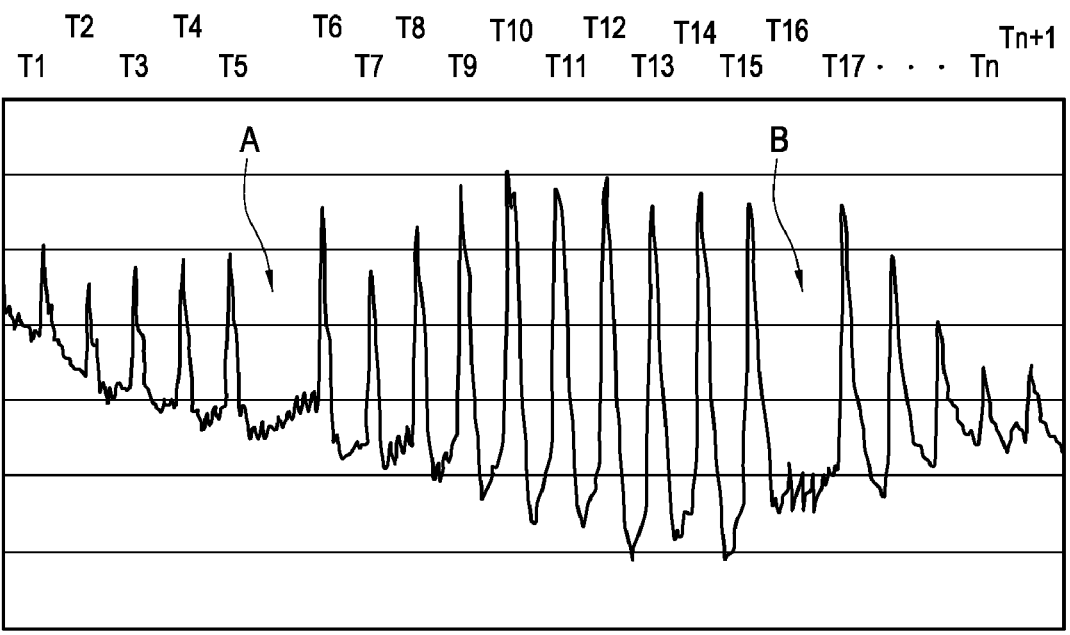
FIG. 4 shows the heartbeat pattern measured by cuff.
Figure 5:
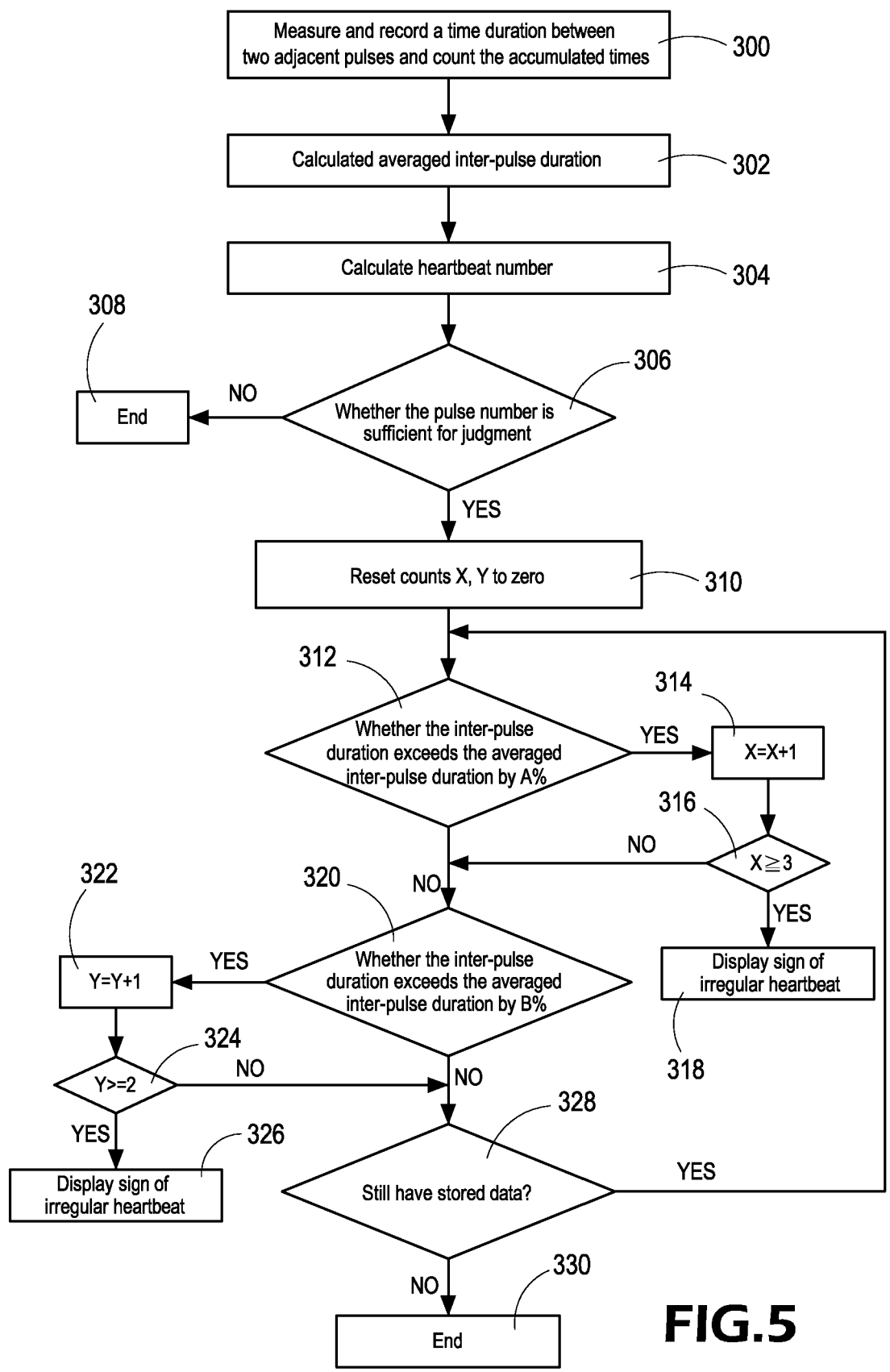
FIG. 5 shows the flowchart of judgment procedure.

FIG. 4 shows the heartbeat pattern measured by cuff. FIG. 5 shows the flowchart of judgment procedure. In step 300, the inter-pulse duration (ΔT) for each pulse is recorded and total pulse numbers are counted. As shown in FIG. 4, the inter-pulse durations A and B have different values with others. Therefore, the inter-pulse time A and B are judged to be inter-pulse duration signal of irregular heartbeat.

Step 302 performs the calculation step to calculate the averaged inter-pulse duration T, where the averaged inter-pulse duration T is the sum of the total inter-pulse duration divided by the total pulse number N, according to formula (1). Step 304 calculates the heartbeat number (H) according to formula (2).

After the pulse duration and the heartbeat number are measured, judgment steps are then performed. A first-stage judgment is first performed, step 306 judges whether the total number of inter-pulse duration is larger than a threshold Z, such as 16 times. When the total number of the inter-pulse duration is smaller than the threshold Z, the procedure is ended at step 308. When the total number of the inter-pulse duration is larger than a threshold Z, a second-stage judgment is performed.

In the second-stage judgment step, there are two conditions for judging the irregular heartbeats. In the first condition, the irregular heartbeat is ensured when the number of inter-pulse duration, which is more than averaged inter-pulse duration by A %, is more than or equal to 3. In the second condition, the irregular heartbeat is ensured when the number of abnormal inter-pulse duration, which is more than averaged inter-pulse duration by B %, is more than or equal to 2. The irregular heartbeat is ensured when either condition is matched.

In the step 310, the counts for the abnormal inter-pulse duration X, Y are reset to zero. Step 312 checks whether an inter-pulse duration is more than the averaged inter-pulse duration by A %. If true, step 314 is performed to increase the count X by one and step 316 is performed to judge whether the count X is more than or equal to 3. If true, step 318 indicates that irregular heartbeat is ensured.

If the first condition is not met, step 320 starts the second condition by judging whether an inter-pulse duration is more than the averaged inter-pulse duration by B %. If true, step 322 is performed to increase the count of Y and step 324 is performed to judge whether the count Y is more than or equal to 2. If true, step 326 indicates that irregular heartbeat is ensured. Step 328 judges whether there is additional heartbeat data to be processed. If true, the procedure is back to step 312, else the procedure is ended at step 330.

In the above-mentioned method, an averaged inter-pulse duration is first obtained by performing measurement for a time period. The averaged inter-pulse duration is then compared with each of the measured inter-pulse durations. In other word, the reference parameter (the averaged inter-pulse duration) and the measured inter-pulse durations are from the same user. Therefore, the method for judging irregular heartbeat according to the present invention can be adapted to different user without the limitation imposed by preset parameter.

Although the present invention has been described with reference to the preferred embodiment thereof, it will be understood that the invention is not limited to the details thereof. Various substitutions and modifications have been suggested in the foregoing description, and other will occur to those of ordinary skill in the art. Therefore, all such substitutions and modifications are intended to be embraced within the scope of the invention as defined in the appended claims.

What is claimed is:

1. A method for judging irregular heartbeat, which is performed on a medical system, the method comprising:
    performing a measurement step to measure a plurality of heartbeat pulses within a time period for a user, and to measure inter-pulse durations and total pulse numbers;
    performing a calculation step to calculate an averaged inter-pulse duration and a heartbeat number;
    performing a judgment step to judge an irregular heartbeat condition by comparing the averaged inter-pulse duration with each inter-pulse duration; and
    performing a display step to show a sign of irregular heartbeat when the irregular heartbeat condition is matched, or show a sign of no irregular heartbeat when the irregular heartbeat condition is not matched,
    wherein the heartbeat number is calculated by dividing 60 with the averaged inter-pulse duration.

2. The method for judging irregular heartbeat as in claim 1, wherein the inter-pulse duration is a time difference between two adjacent pulses.

3. The method for judging irregular heartbeat as in claim 1, wherein the averaged inter-pulse duration is calculated by summing all inter-pulse durations and divided by the total pulse number.

4. The method for judging irregular heartbeat as in claim 1, wherein the judgment step further comprises:
    performing a first-stage judgment to compare the number of inter-pulse duration with a first predetermined threshold; and
    performing a second-stage judgment when the first-stage judgment is matched, wherein the second-stage judgment compares a number of abnormal inter-pulse duration with another predetermined threshold.

5. The method for judging irregular heartbeat as in claim 4, wherein the first-stage judgment for irregular heartbeat compares a number of inter-pulse durations with a first threshold.

6. The method for judging irregular heartbeat as in claim 4, wherein the second-stage judgment for irregular heartbeat finds a number of abnormal inter-pulse durations, which exceeds the averaged inter-pulse duration by a predetermined ratio, wherein the second-stage judgment is matched when the number of abnormal inter-pulse durations is more than a predetermined count.

7. A method for judging irregular heartbeat, which is performed on a medical system, the method comprising:
    performing a measurement step to measure a plurality of heartbeat pulses within a time period for a user, and to measure inter-pulse durations and total pulse numbers;
    performing a calculation step to calculate an averaged inter-pulse duration and a heartbeat number;
    performing a judgment step to judge an irregular heartbeat condition by comparing the averaged inter-pulse duration with each inter-pulse duration; and
    performing a display step to show a sign of irregular heartbeat when the irregular heartbeat condition is matched, or show a sign of no irregular heartbeat when the irregular heartbeat condition is not matched,
    wherein the judgment step further comprises:

performing a first-stage judgment to compare the number of inter-pulse duration with a first predetermined threshold; and performing a second-stage judgment when the first-stage judgment is matched, wherein the second-stage judgment compares a number of abnormal inter-pulse duration with another predetermined threshold.

8. The method for judging irregular heartbeat as in claim 7, wherein the inter-pulse duration is a time difference between two adjacent pulses.

9. The method for judging irregular heartbeat as in claim 7, wherein the averaged inter-pulse duration is calculated by summing all inter-pulse durations and divided by the total pulse number.

10. The method for judging irregular heartbeat as in claim 7, wherein the heartbeat number is calculated by dividing 60 with the averaged inter-pulse duration.

11. The method for judging irregular heartbeat as in claim 7, wherein the first-stage judgment for irregular heartbeat compares a number of inter-pulse durations with a first threshold.

12. The method for judging irregular heartbeat as in claim 7, wherein the second-stage judgment for irregular heartbeat finds a number of abnormal inter-pulse durations, which exceeds the averaged inter-pulse duration by a predetermined ratio, wherein the second-stage judgment is matched when the number of abnormal inter-pulse durations is more than a predetermined count.

* * * * *